US011389205B2

(12) United States Patent
Corbin et al.

(10) Patent No.: US 11,389,205 B2
(45) Date of Patent: Jul. 19, 2022

(54) SPINAL FASTENER WITH SERRATED THREAD

(71) Applicant: Stryker European Operations Holdings LLC, Kalamazoo, MI (US)

(72) Inventors: Erika Corbin, Mahwah, NJ (US); Lori Dombrowski, Elmwood Park, NJ (US); Charles L. Bush, Jr., Wayne, NJ (US); Paul R. Rochette, Stanhope, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 0 days.

(21) Appl. No.: 15/645,264

(22) Filed: Jul. 10, 2017

(65) Prior Publication Data

US 2018/0146987 A1 May 31, 2018

Related U.S. Application Data

(60) Provisional application No. 62/428,103, filed on Nov. 30, 2016.

(51) Int. Cl.
*A61B 17/70* (2006.01)
*A61B 17/86* (2006.01)

(52) U.S. Cl.
CPC ...... *A61B 17/7032* (2013.01); *A61B 17/7037* (2013.01); *A61B 17/86* (2013.01); *A61B 17/863* (2013.01); *A61B 17/8625* (2013.01)

(58) Field of Classification Search
CPC .............. A61B 17/8625; A61B 17/863; A61B 17/8635; F16B 5/02; F16B 39/00; F16B 39/22; F16B 39/282; A61C 8/0022; A61C 8/0024; A61C 8/0025

USPC ......... 606/300–321, 265; 411/307, 308, 378, 411/387.5–387.8, 417–422

See application file for complete search history.

(56) References Cited

U.S. PATENT DOCUMENTS

| 2,135,637 | A | 11/1938 | Gade |
| 2,200,227 | A | 5/1940 | Olson |
| 3,083,609 | A | 4/1963 | Lovisek |
| 3,858,942 | A | 1/1975 | Humlong |
| 4,468,200 | A | 8/1984 | Munch |

(Continued)

FOREIGN PATENT DOCUMENTS

| EP | 0714643 A1 | 6/1996 |
| EP | 2668925 A1 | 12/2013 |

(Continued)

OTHER PUBLICATIONS

Documents cited or considered relevant in Original Search from the Australian Patent Office for Application No. 2017245342 dated Feb. 20, 2018.

(Continued)

*Primary Examiner* — Eduardo C Robert
*Assistant Examiner* — Christina Negrellirodriguez
(74) *Attorney, Agent, or Firm* — Lerner, David, Littenberg, Krumholz & Mentlik, LLP

(57) ABSTRACT

A fastener configured for spinal applications includes a head having a channel adapted to receive a spinal rod and a shaft extending from the head to a distal tip and having a thread, at least a portion of the thread being serrated. The serrated portion of the thread includes peaks and troughs and can extend along about 35 percent of a length of the thread.

20 Claims, 20 Drawing Sheets

(56) References Cited

U.S. PATENT DOCUMENTS

| | | |
|---|---|---|
| 4,516,893 A | 5/1985 | Barth |
| 4,637,767 A | 1/1987 | Yaotani et al. |
| 4,842,467 A | 6/1989 | Armstrong |
| 4,863,383 A | 9/1989 | Grafelmann |
| 5,044,853 A | 9/1991 | Dicke |
| 5,110,245 A | 5/1992 | Hiroyuki |
| 5,427,527 A | 6/1995 | Niznick et al. |
| 5,460,467 A | 10/1995 | Dessouroux |
| 5,716,358 A | 2/1998 | Ochoa et al. |
| 5,827,030 A | 10/1998 | Dicke |
| 5,897,280 A | 4/1999 | Dicke |
| 6,056,491 A | 5/2000 | Hsu |
| 6,086,302 A | 7/2000 | Gerhard |
| 6,152,666 A | 11/2000 | Walther et al. |
| 6,254,327 B1 | 7/2001 | Chen |
| 6,296,642 B1 | 10/2001 | Morrison et al. |
| 6,386,877 B1 | 5/2002 | Sutter |
| 6,679,701 B1 | 1/2004 | Blacklock |
| 6,926,484 B2 | 8/2005 | Kram et al. |
| 7,087,057 B2 | 8/2006 | Konieczynski et al. |
| 7,160,073 B2 | 1/2007 | Mizuno et al. |
| 7,163,366 B2 | 1/2007 | Chen |
| 7,273,373 B2 | 9/2007 | Horiuchi |
| 7,677,851 B2 | 3/2010 | Desai et al. |
| 7,798,756 B2 | 9/2010 | Chang |
| 7,806,693 B2 | 10/2010 | Hurson |
| 8,062,270 B2 | 11/2011 | Sweeney |
| 8,221,119 B1 | 7/2012 | Valen |
| 8,267,966 B2 | 9/2012 | McCormack et al. |
| 8,360,702 B2 | 1/2013 | Yu |
| 8,372,152 B2 | 2/2013 | Kirschman |
| 8,518,090 B2 | 8/2013 | Huebner et al. |
| 8,635,894 B2 | 1/2014 | Christ |
| 8,904,622 B2 | 12/2014 | Kochheiser |
| 9,572,599 B1 | 2/2017 | Casey et al. |
| 10,039,572 B2 | 8/2018 | Harris et al. |
| D857,898 S | 8/2019 | Loftus |
| D898,196 S | 10/2020 | Corbin et al. |
| D926,983 S | 8/2021 | Corbin et al. |
| 2003/0031528 A1 | 2/2003 | Kram et al. |
| 2004/0101381 A1 | 5/2004 | Kram et al. |
| 2004/0220575 A1 | 11/2004 | Biedermann et al. |
| 2006/0155277 A1 | 7/2006 | Metz-Stavenhagen |
| 2008/0014556 A1 | 1/2008 | Neumeyer |
| 2008/0038693 A1 | 2/2008 | Hansson |
| 2008/0166201 A1 | 7/2008 | Desai et al. |
| 2008/0249579 A1* | 10/2008 | Taylor .................. A61B 17/863 606/317 |
| 2008/0269809 A1* | 10/2008 | Garamszegi ....... A61B 17/7037 606/305 |
| 2011/0060373 A1 | 3/2011 | Russell et al. |
| 2011/0087288 A1 | 4/2011 | Stevenson et al. |
| 2011/0190830 A1 | 8/2011 | Biedermann et al. |
| 2011/0217145 A1 | 9/2011 | Kochheiser et al. |
| 2012/0083847 A1 | 4/2012 | Huebner et al. |
| 2012/0158137 A1 | 6/2012 | Pinczewski |
| 2013/0006364 A1 | 1/2013 | McCormack et al. |
| 2013/0053901 A1 | 2/2013 | Cormier et al. |
| 2014/0025124 A1 | 1/2014 | Champagne et al. |
| 2014/0058460 A1 | 2/2014 | Reed |
| 2014/0094859 A1 | 4/2014 | Reed |
| 2014/0236245 A1 | 8/2014 | Hainard |
| 2014/0277193 A1 | 9/2014 | Mobasser et al. |
| 2015/0052735 A1 | 2/2015 | Kochheiser |
| 2015/0230844 A1 | 8/2015 | Ellis |
| 2015/0272646 A1 | 10/2015 | Russell |
| 2015/0282844 A1 | 10/2015 | Vedula et al. |
| 2016/0015483 A1* | 1/2016 | Kumar ................. A61C 8/0068 606/301 |
| 2016/0213413 A1 | 7/2016 | Hientzsch et al. |
| 2016/0310182 A1 | 10/2016 | Sixto et al. |
| 2016/0310187 A1 | 10/2016 | Leibinger et al. |
| 2018/0146987 A1 | 5/2018 | Corbin et al. |
| 2018/0368898 A1 | 12/2018 | DiVincenzo et al. |
| 2019/0219090 A1 | 7/2019 | Stager |

FOREIGN PATENT DOCUMENTS

| | | |
|---|---|---|
| FR | 2788215 A1 | 7/2000 |
| JP | H08238256 A | 9/1996 |
| JP | 2003290245 A | 10/2003 |
| JP | 2004329883 A | 11/2004 |
| JP | 2005127487 A | 5/2005 |
| JP | 2011500292 A | 1/2011 |
| JP | 2011244906 A | 12/2011 |
| JP | 2014508550 A | 4/2014 |
| JP | 2014529446 A | 11/2014 |
| JP | 2015531282 A | 11/2015 |
| JP | 6596056 B2 | 10/2019 |
| WO | 2016006598 A1 | 1/2016 |

OTHER PUBLICATIONS

European Search Report for EP Application No. 17200878 dated Apr. 17, 2018.

* cited by examiner

SPINAL FASTENER WITH SERRATED THREAD

CROSS-REFERENCE TO RELATED APPLICATIONS

The present application claims the benefit of the filing date of U.S. Provisional Patent Application No. 62/428,103 filed Nov. 30, 2016, the disclosure of which is hereby incorporated herein by reference.

BACKGROUND OF THE INVENTION

The present invention generally relates to spinal fixation devices, and more particularly to spinal fasteners having serrated threads.

A technique commonly referred to as spinal fixation is employed for fusing together and/or mechanically immobilizing vertebrae of the spine. Spinal fixation may also be used to alter the alignment of adjacent vertebrae relative to one another so as to change the overall alignment of the spine. Such techniques have been used effectively to treat many degenerative conditions and, in most cases, to relieve pain suffered by the patient.

In some applications, a surgeon will install pedicle screws into the pedicles of adjacent vertebrae (along one or multiple levels of the spine) and thereafter connect the screws with a spinal rod in order to provide immobilization and stabilization of the vertebral column. Whether conducted in conjunction with interbody fusion or across single or multiple levels of the spine, the use of pedicle screws connected by fixation rods is an important treatment method employed by spinal surgeons.

Some surgeons insert pedicle screws via powered screw insertion, while other surgeons prefer manual screw insertion. For the surgeons that opt for manual screw insertion, surgeon fatigue and bone fracturing can be significant problems during surgery. Surgeon fatigue can adversely affect the accuracy of the insertion process and the depth to which the screws are inserted within the pedicle bone.

There remains room for improvement in the design and use of pedicle screws, particularly in the case of manual insertion so that related surgical procedures can be performed with greater efficiency and consistency.

BRIEF SUMMARY OF THE INVENTION

A first aspect of the present invention is a fastener having a head including a channel adapted to receive a spinal rod and a shaft extending from the head to a distal tip and including a thread, at least a portion of the thread being serrated.

In other embodiments according to the first aspect, the shaft has a longitudinal axis and an angle between the longitudinal axis and thread may vary along a length of the shaft. The serrated portion of the thread may include serrations having a width that increases along a portion of a length of the thread toward the distal tip. The shaft may be cannulated. The head may be polyaxially movable with respect to the shaft. The shaft may be tapered. Further, the taper of the shaft measured by a line over a surface of the thread at points on two or more revolutions of the thread may be between 16 and 20 degrees relative to the longitudinal axis of the shaft. The serrated portion of the thread may include serrations having a width that decreases over a part of the serrated portion toward the distal tip. The thread may include walls disposed between the shaft and a surface of the serrations, the walls angled so that walls adjacent to one another along the longitudinal axis are at a 55 to 65 degree angle with respect to each other. The head may be monoaxially attached to the shaft.

A second aspect of the invention is a fastener having a head including a channel adapted to receive a spinal rod, a shaft coupled with the head, the shaft including a distal tip, a thread extending between the head and the distal tip, and a serration extending along at least a portion of the thread, the serration including peaks and troughs.

In other embodiments according to the second aspect, the peaks at a radial distance to the longitudinal axis of the shaft greater than a radial distance to the longitudinal axis of the shaft from the troughs adjacent to the peak, the teeth may have a width measured parallel to the troughs such that the width may be greater at the troughs than at the peaks. The peaks of the teeth may include a first type defined by an edge at an abutment between surfaces connecting the peak with adjacent troughs and a second type defined by a planar surface. The serration may include a progressively increasing pitch from the tip toward the head. The first peak may vary in height along a length of the thread so that a first short peak with a first radius measured from the longitudinal axis of the shaft may be adjacent to a first tall peak with a second radius, which in turn may be adjacent to a second short peak with a third radius, adjacent to a second tall peak with a fourth radius, the first and third radii may be similar and may both be lesser in dimension than the second and fourth radii.

The peaks may extend along helical curves winding around the shaft in a direction opposite to a helical curve along which the thread extends. The peaks may extend along axes that are parallel to or aligned with a longitudinal axis of the shaft. The shaft may include a cutting flute that extends in a linear direction along an axis angled with respect to a longitudinal axis of the shaft. The shaft may include a cutting flute that extends along a helical path from the distal tip of the shaft.

A third aspect of the fastener is a fastener having a head including a channel adapted to receive a spinal rod, a shaft coupled to the head, the shaft including a distal tip, a thread extending between the head and the distal tip, and a serration extending along approximately 35 percent of a length of the thread. In other embodiments according to the third aspect, the serration may include peaks and troughs. The distal tip may taper such that an angle between an axis measured from a first point on a surface of the thread at a first end of the taper to a second point at the tip of the fastener on the longitudinal axis of the shaft may be approximately 20 to 30 degrees relative to the longitudinal axis of the shaft.

DETAILED DESCRIPTION

Figure 1:
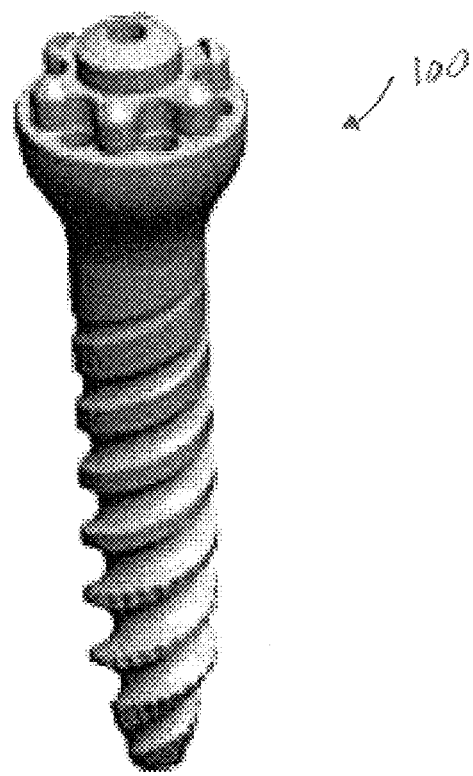
FIG. 1 is a perspective view of a fastener in accordance with a first embodiment of the present invention.

The present invention relates to a fastener to be used in conjunction with spinal rods during spinal surgery. Those of skill in the art will recognize that the following description is merely illustrative of the principles of the invention, which may be applied in various ways to provide many different alternative embodiments.

FIGS. 1-6 depict a first embodiment of a fastener 100 that is configured for spinal applications, and in particular, for use as a pedicle screw or fastener. Fastener 100 includes a screw body 101 and a tulip, which has a channel adapted to receive a spinal rod. A spinal rod can be installed into the tulip and held in place by a set screw (not shown), which is threaded into internal threads of the tulip. While the tulip is not shown in FIGS. 1-6, tulips are featured in the embodiments shown in FIGS. 10-13, described below.

Fastener 100 is poly-axial in that screw body 101 is separate from the tulip. The tulip and proximal end of the screw body can generally be referred to as a head of fastener 100. Screw body 101 includes a shaft 103 that extends along a longitudinal axis 108 from a proximal portion 102 or a head of fastener 100 to a distal tip 105. The tulip is polyaxially movable (i.e., a polyaxial pedicle screw) with respect to proximal portion 102 of screw body 101. Proximal end 102 of screw body 101 forms an interference fit connection with a distal opening of the tulip to create the poly-axial connection. The tulip can swivel about and form different angles with screw body 101 to facilitate proper rod placement. In other embodiments, the fastener can be a monolithic structure (i.e., a monoaxial pedicle screw) having the tulip statically connected with the proximal end of the screw body. Both of such embodiments may additionally have retractor blades extending from the tulip, such as those described below in connection with FIG. 12.

Figure 2:
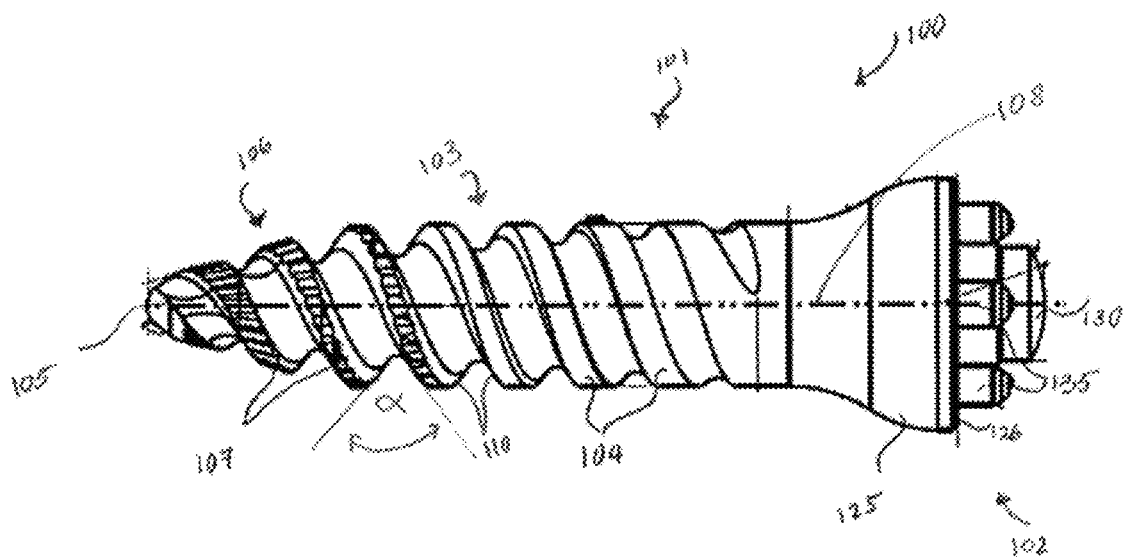
FIG. 2 is a front plan view of the fastener of FIG. 1.
Figure 3:
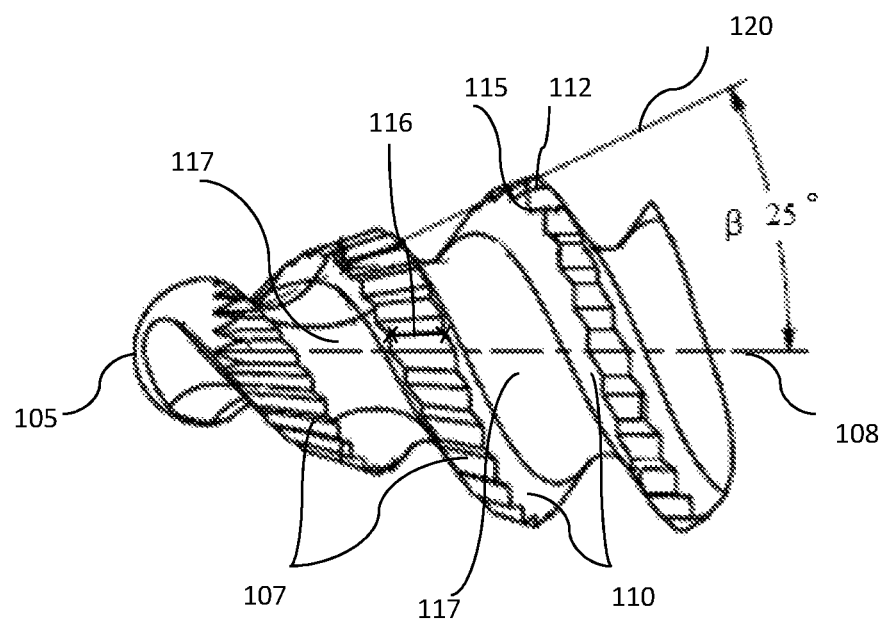
FIG. 3 is an enlarged front plan view of a distal portion of the fastener of FIG. 1.

Shaft 103 includes a thread 104 extending between proximal portion 102 and distal tip 105. Beginning thread 104 at distal tip 105 allows shaft 103 to engage and anchor into the bone immediately upon contact. As seen in FIGS. 1-3, thread 104 includes along a length thereof a serrated portion 106 that has individual serrations 107. Serrated portion 106 extends along about 35 to 40 percent of a length of thread 104. In certain embodiments, serrated portion 106 extends along 35 percent of the length of thread 104. In other embodiments, the range of serrated portion 106 can be about 25-45 percent of a length of thread 104, about 20-50 percent of a length of thread 104, or about 10-60 percent of a length of thread 104. This ratio of the serrated portion to the overall thread length allows for a consistent feel during manual insertion, regardless of the screw length. The inclusion of serrated portion 106 provides a solution for the problems of the prior art, as described above. Serrations 107 reduce insertion torque, thereby improving ease of insertion, while not compromising pullout strength. Serrated screws also allow for a quicker insertion time. The reduced insertion torque reduces the chance of bone fracturing and breaching. Additionally, serrations 107 allow surgeons to retain tactile feedback with minimized energy exertion resulting in greater accuracy during positioning of fastener 100, as compared with manual screw insertion of other non-serrated prior art screws.

Shaft 103 is tapered, such that the tapered portion of shaft 103 is defined by an angle of between 16 and 20 degrees measured between longitudinal axis 108 of the shaft 103 and an axis intersecting outer surfaces of thread 104 at two or more revolutions of thread 104. In certain embodiments, the tapered portion of shaft 103 extends along about 35 percent of the length of thread 104, which can match the length of thread 104 along which serrated portion 106 extends. In other embodiments, the range of tapered portion can be about 25-45 percent of a length of thread 104, about 20-50 percent of a length of thread 104, or about 10-60 percent of a length of thread 104. This configuration is designed so that once a maximum diameter of the threads is reached, the serrated portion 106 ends so that the threads at the maximum diameter do not continue to cut into the bone. Further cutting into the bone by the maximum diameter threads can weaken the engagement between the later-inserted, non-serrated threads and the bone, which reduces tactile feedback to the user. Having the tapered portion of shaft 103 and serrated portion 106 both extend along the same amount of the length of thread 104 (i.e., about 35 percent) allows some resistance at all times during insertion of the screw, which is desirable. Other embodiments in accordance with the present invention may include a shaft that is not tapered.

Figure 4:
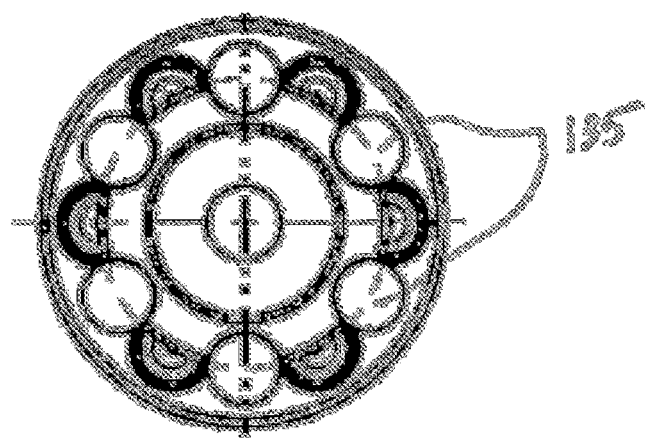
FIG. 4 is a top plan view of the fastener of FIG. 1.
Figure 5:
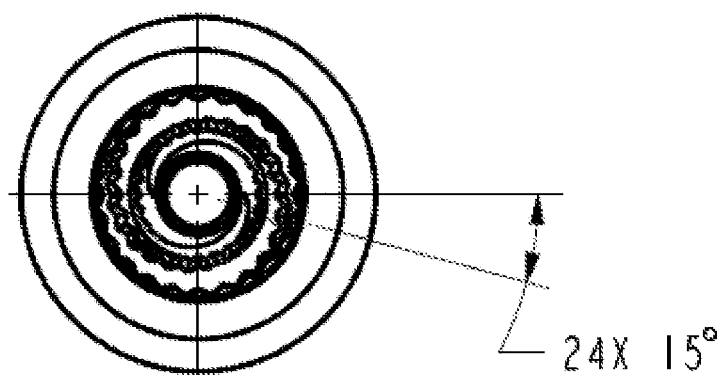
FIG. 5 is a bottom plan view of the fastener of FIG. 1.

In the embodiment of FIGS. 1-6, proximal portion 102 of screw body 101 includes a proximally-facing flat top surface 126 and a distally-facing, generally spherical surface 125, which interfaces with the tulip to allow for polyaxial movement between the tulip and screw body 101. As shown in FIGS. 1, 2, and 4, proximal portion 102 includes a projection 130 extending from a central portion of flat top surface 126. Proximal portion 102 further includes nubs 135 extending from flat top surface 126 at locations around the periphery thereof and surrounding projection 130. Nubs 135 are each smaller in size than projection 130. Although the shape of projections 130 and nubs 135 can vary depending on the corresponding tulip assembly and the corresponding insertion instruments, in the illustrated embodiment, projections 130 and nubs 135 are each rounded to have generally spherically-shaped proximal ends. As shown more clearly in FIG. 2, in this embodiment, proximal portion 102 includes six nubs 135. The number of nubs 135 can vary in other embodiments.

Thread 104 can have one or more of many cross-sectional areas, such as trapezoidal, square, triangular, rectangular or any other shape known in the art. As shown in FIGS. 2 and 3, thread 104 includes sidewalls 110 on either side that extend from an inner diameter of shaft 103 to an outer diameter of thread 104. Sidewalls 110 are angled such that sidewalls 110 that face one another along the longitudinal axis 108 of shaft 103 form an angle α therebetween of 60 degrees. Angle α can be about 60 degrees, as in the depicted embodiment, while it can range between about 55-65 degrees in other embodiments. In still other embodiments, angle α can range between about 45-75 degrees, and between about 40-80 degrees in other embodiments. Thread 104 is configured such that an angle between sidewall 110 and longitudinal axis 108 of shaft 103 varies along a length of the shaft 103. That is, the angle between the sidewall of thread 104 and longitudinal axis 108 varies along the path of thread 104. In other embodiments, the angle of sidewall 110 can be constant. In the embodiment shown in FIGS. 1-6, sidewalls 110 extend toward longitudinal axis 108 until they intersect with a concave, helical path between adjacent passes of thread 104, with the helical path containing the inner diameter of shaft 103. In other embodiments, sidewalls 110 may extend to the inner diameter of the shaft by intersecting or by the helical path between adjacent passes of thread 104 being flat instead of concave.

As shown in FIG. 2, thread 104 includes serrated portion 106 at a distal end of shaft 103 that continuously transitions into a smooth, non-serrated portion at a proximal end of shaft 103. Serrations 107 are geometrical cut-outs along serrated portion 106 that allow for easier insertion of fastener 100 into the pedicle bone by reducing the insertion torque. This reduction in torque limits surgeon fatigue and reduces the chance of fracturing or breaching of the pedicle bone.

Referring to FIG. 3, thread 104 has a tapered portion that defines a tapered angle β measured between longitudinal axis 108 of shaft 103 and an axis 120 intersecting distal tip 105 and an outer surface of thread 104 at a proximal end of the tapered portion of thread 104. Angle β is 25 degrees in the depicted embodiment. In other embodiments, angle β can be about 25 degrees, or between about 20 to 30 degrees. In still other embodiments, angle β can range between about 15-35 degrees, and between about 10-40 degrees in other embodiments.

Referring to FIGS. 3 and 4, serrated portion 106 include peaks 112 and troughs 115 that alternate along serrated portion 106 to define serrations 107. Peaks 112 are triangular in shape looking along the longitudinal axis 108. Serrations 107 further include respective thicknesses 116 measured parallel to longitudinal axis 108 of shaft 103 such that successive thicknesses 116 increase in magnitude along a portion of a length of thread 104 toward distal tip 105. Each thickness 116 is measured from the distal end to the proximal end of each serration 107. In other embodiments, successive thicknesses can decrease in magnitude along a portion of a length of thread 104 toward distal tip 105 or can remain constant.

In the embodiment of FIGS. 1-6, each peak 112 is disposed at a radial distance from longitudinal axis 108 of shaft 103 that is greater than a radial distance from longitudinal axis 108 of shaft 103 to an adjacent trough 115. Each peak 112 has a thickness measured parallel to longitudinal axis 108 of shaft 103 that is less than a thickness measured parallel to longitudinal axis 108 of shaft 103 of an adjacent trough 115. In other words, due to the angle between sidewalls 110 of thread 104 and/or curvature of surfaces 117 of shaft 103, the thickness is greater at the troughs 115 than at the adjacent peaks 112.

Serrations 107 include respective widths measured perpendicular to longitudinal axis 108 of shaft 103, such that successive widths decrease in magnitude along a portion of a length of thread 104 toward the distal tip 105. In other embodiments, successive widths can increase in magnitude along a portion of a length of thread 104 toward distal tip 105 or can remain constant.

Figure 6:
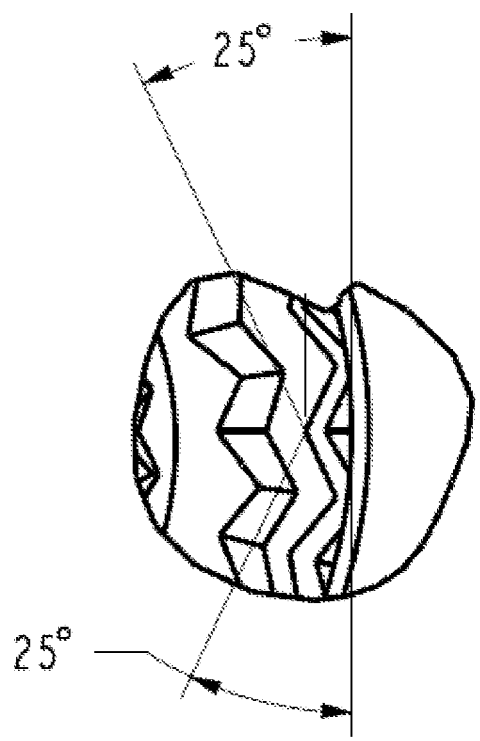
FIG. 6 is an enlarged bottom plan view of a portion of the fastener of FIG. 1.

The pitch of a serration 107 is the distance between adjacent troughs 115 that define the serration 107, that is, from a first trough 115 across a peak 112 to an adjacent second trough 115. In the embodiment shown in FIGS. 1-6, the pitch of the respective serrations 107 progressively and incrementally increases from distal tip 105 toward proximal portion 102 of shaft 103. Thus, the pitch of a serration 107 nearer the distal tip 105 is less than the pitch of a serration 107 closer to the proximal portion 102. The number of serrations 107 per revolution of thread 104 is constant, as shown in FIG. 6 in a view from distal tip 105 toward proximal portion 102 of shaft 103. This results in the small pitch of a serration 107 nearer the distal tip 105 because more serrations are fit into a revolution of thread 104 that has a generally smaller diameter due to its tapered structure. Different angles of the tapered section of thread 104 provide differently shaped serrations 107. In one embodiment, the angle of each face of serration 107 measured from a plane through adjacent troughs 115 is 25 degrees. In other embodiments, the angle of each face of serration 107 measured from a plane through adjacent troughs 115 is between 20-30 degrees, and between about 10-40 degrees in other embodiments.

Figure 7:
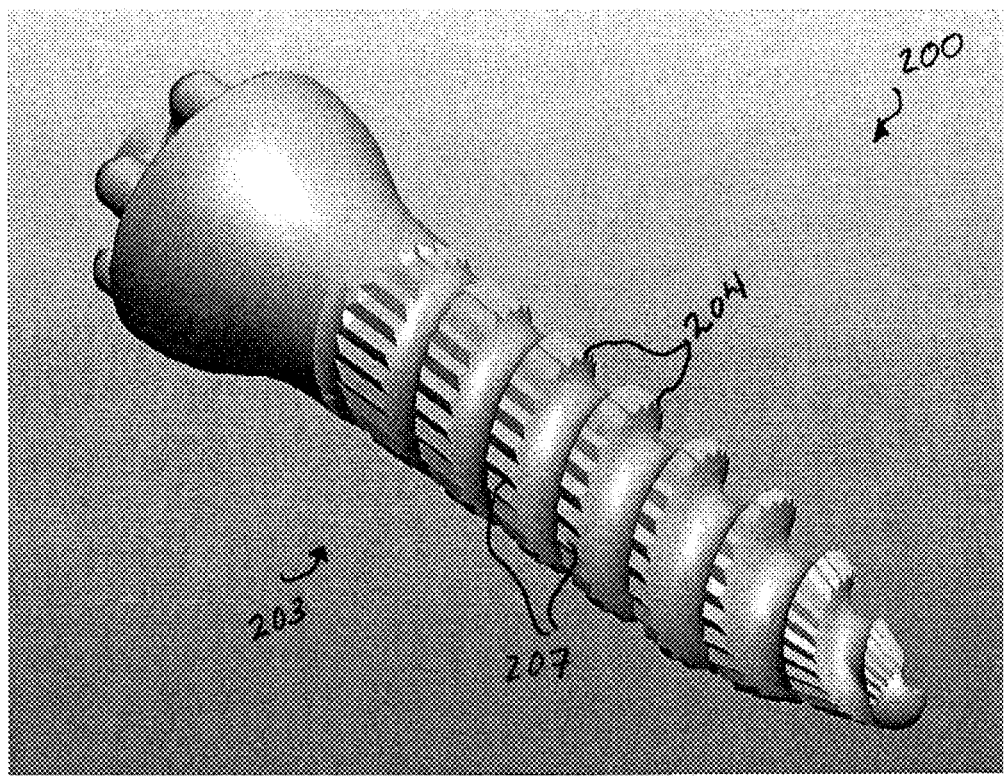
FIG. 7 is a perspective view of a fastener in accordance with another embodiment of the present invention.
Figure 8:
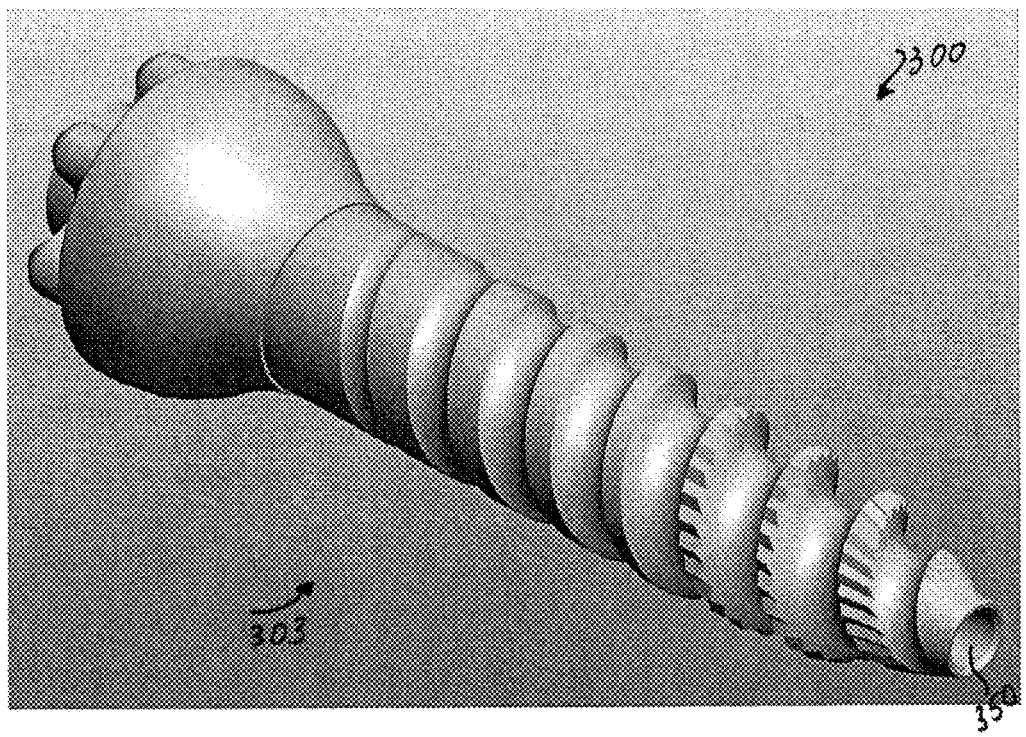
FIG. 8 is a perspective view of a fastener in accordance with another embodiment of the present invention.

Other embodiments of fasteners in accordance with the present invention are shown in FIGS. 7 and 8, respectively. Fastener 200 is shown in FIG. 7 with serrations 207 running the entire length of thread 204 along shaft 203. Fastener 300 is shown in FIG. 8 having a cannulated shaft 303 that defines a passage 350 along the length of shaft 303. Passage 350 can extend along a full length of fastener 300 so that it is accessible at both the proximal and distal ends thereof, with the distal opening being shown in FIG. 7. The proximal opening corresponds with the central projection at the proximal portion of fastener 300.

FIGS. 9A-9I each depict different embodiments having a varying number of serrations per each thread revolution. In each embodiment, the pitch incrementally increases from the distal tip to the proximal portion. For example, in the fastener 400 shown in FIG. 9A, there are seventy-two (72) peaks 412 per revolution of thread 404. The pitch is smaller at the distal tip 405 than on threads 404 closer to the proximal portion 402 due to the tapered nature of the screw to allow for the same number of peaks per revolution of threads 404.

Figure 9A:
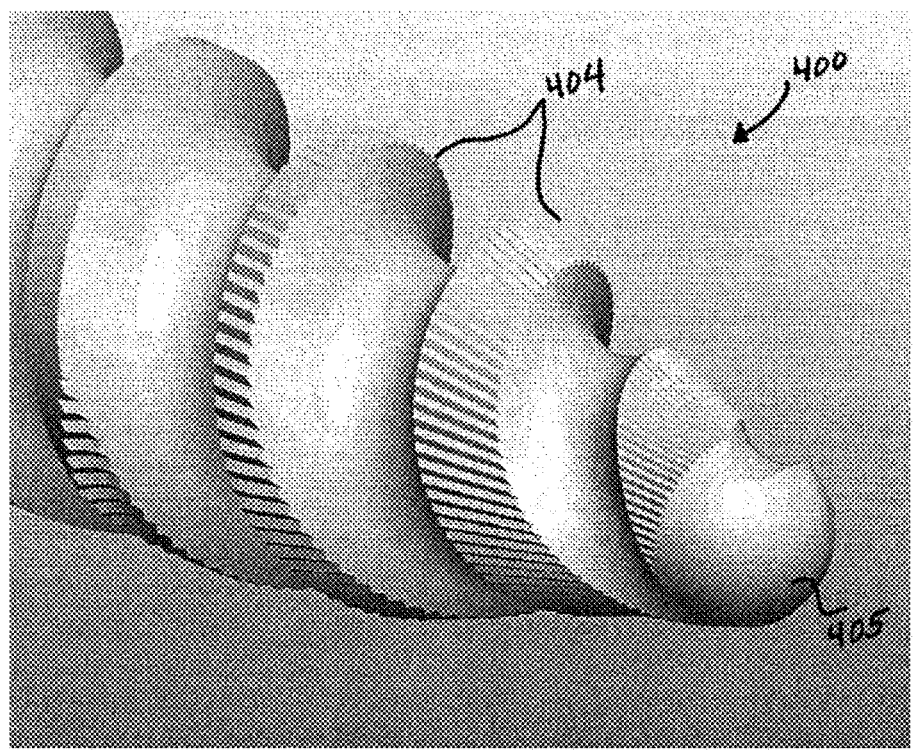
FIGS. 9A-9Q are perspective views of distal portions of other embodiments of fasteners in accordance with the present invention.
Figure 9B:
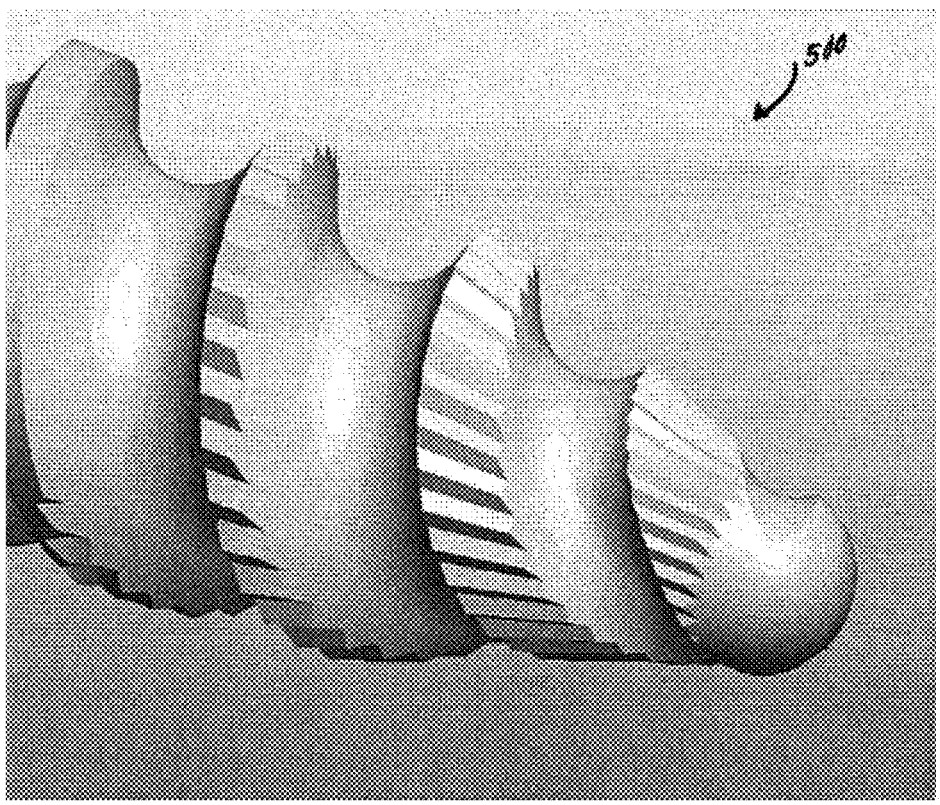
Figure 9C:
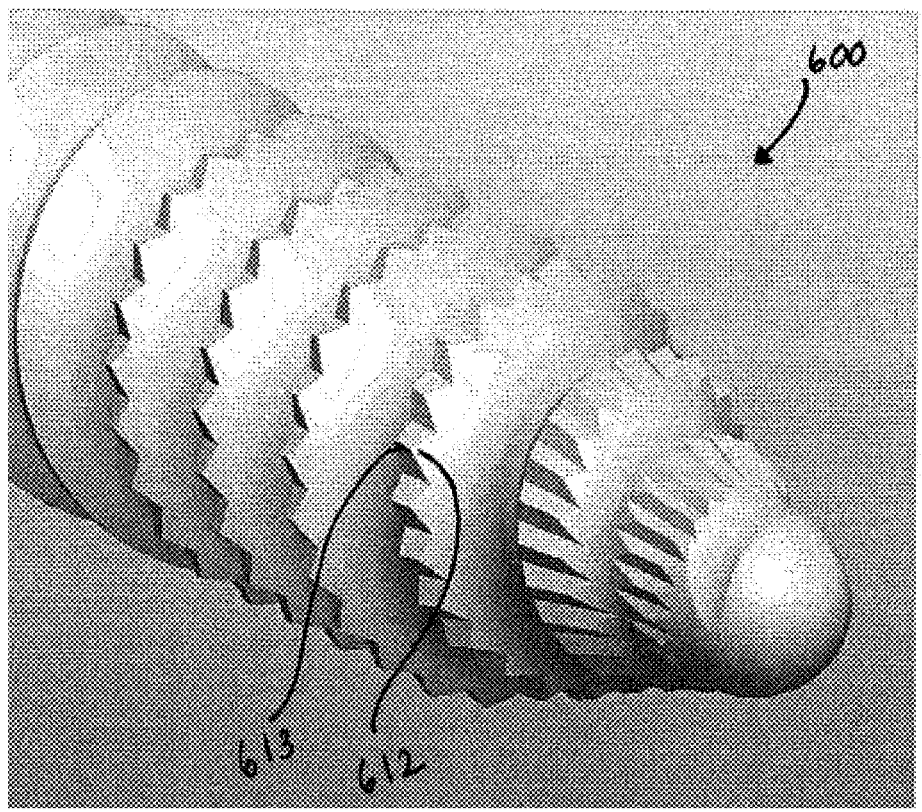
Figure 9D:
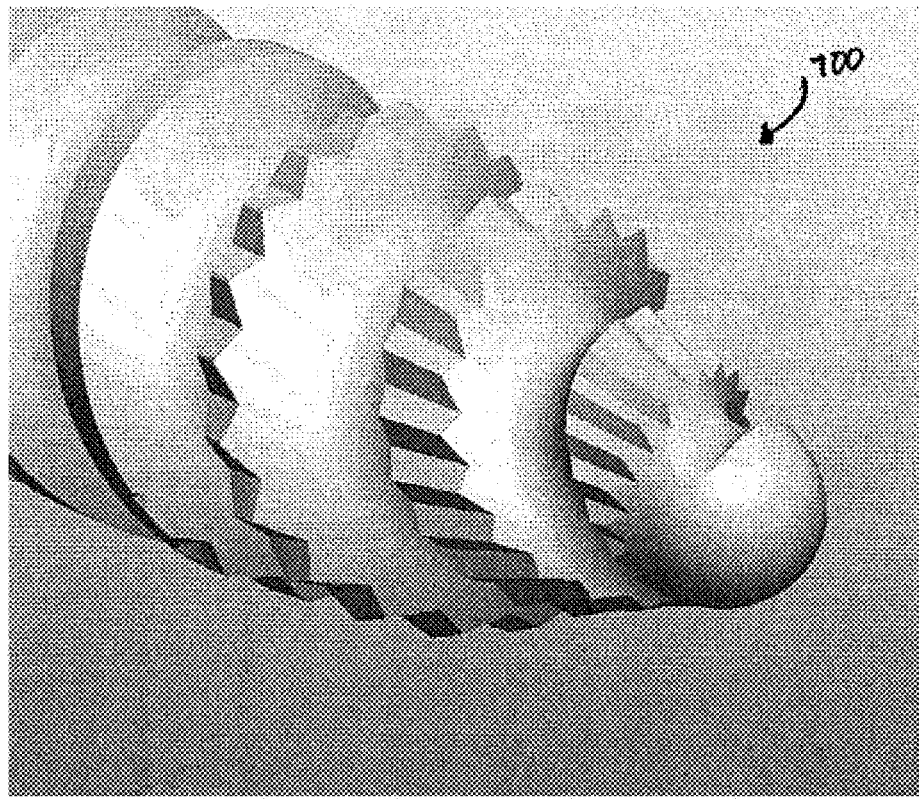
Figure 9E:
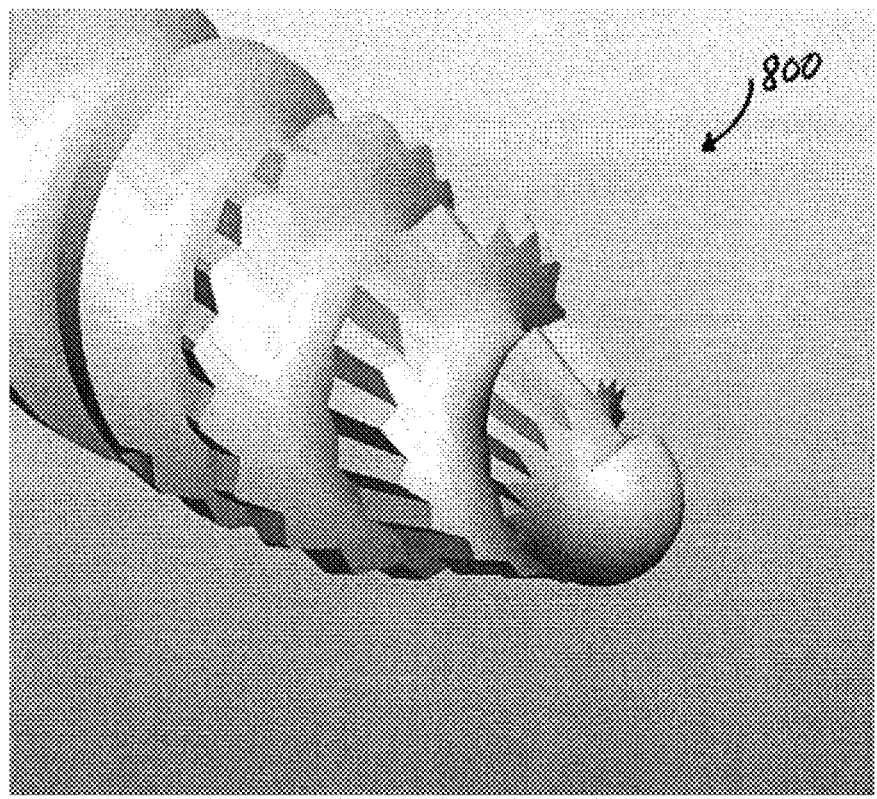
Figure 9F:
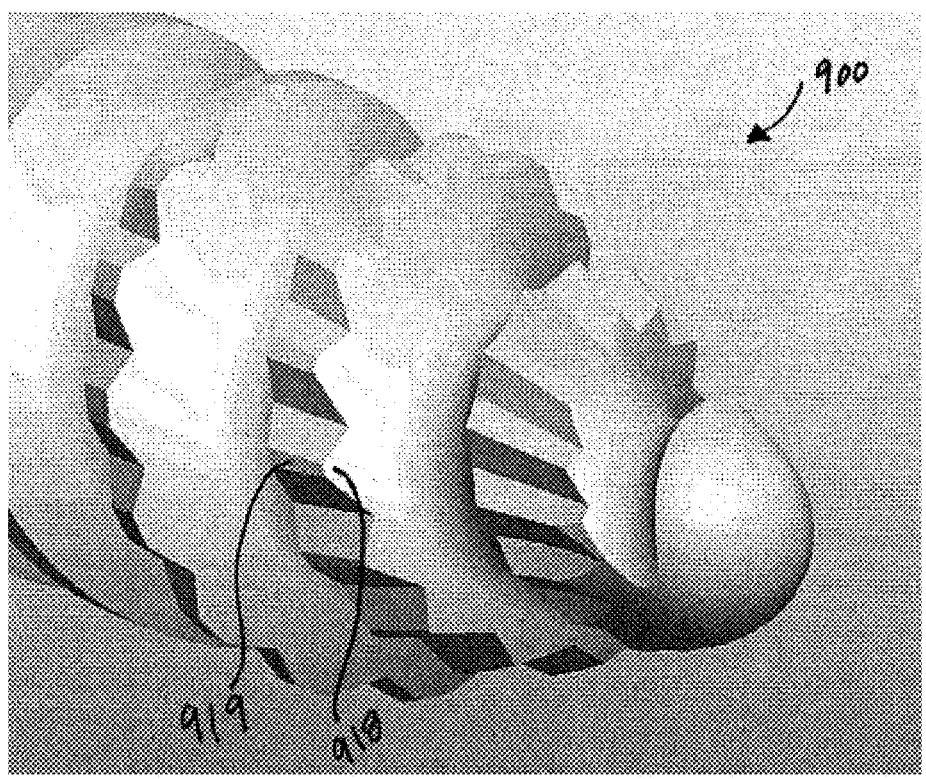
Figure 9G:
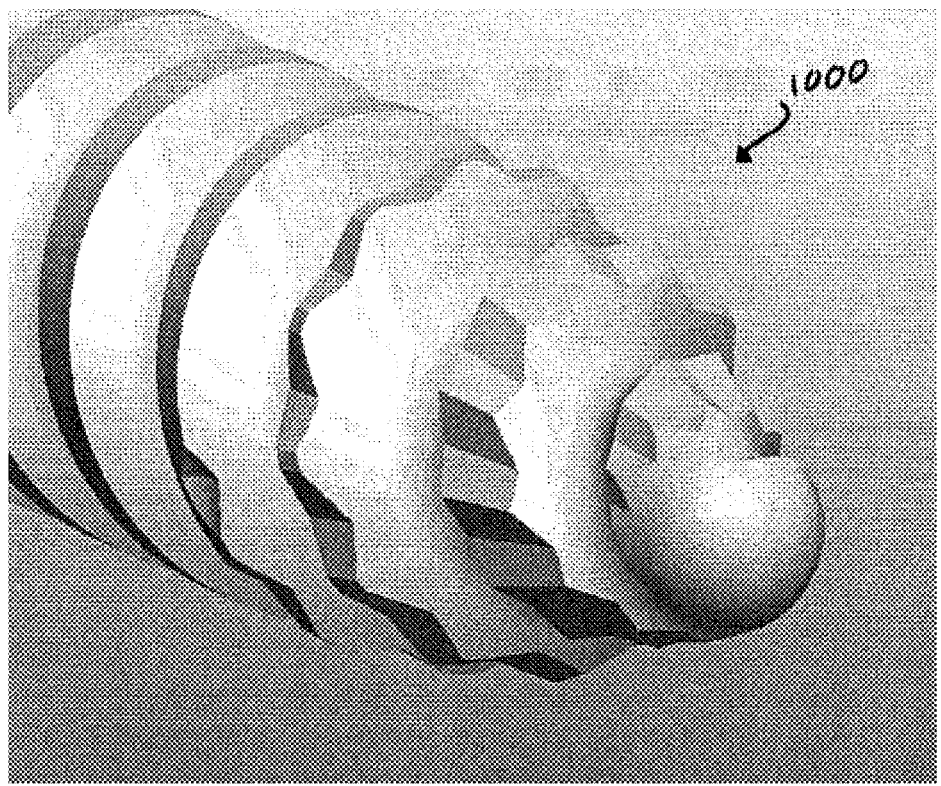
Figure 9H:
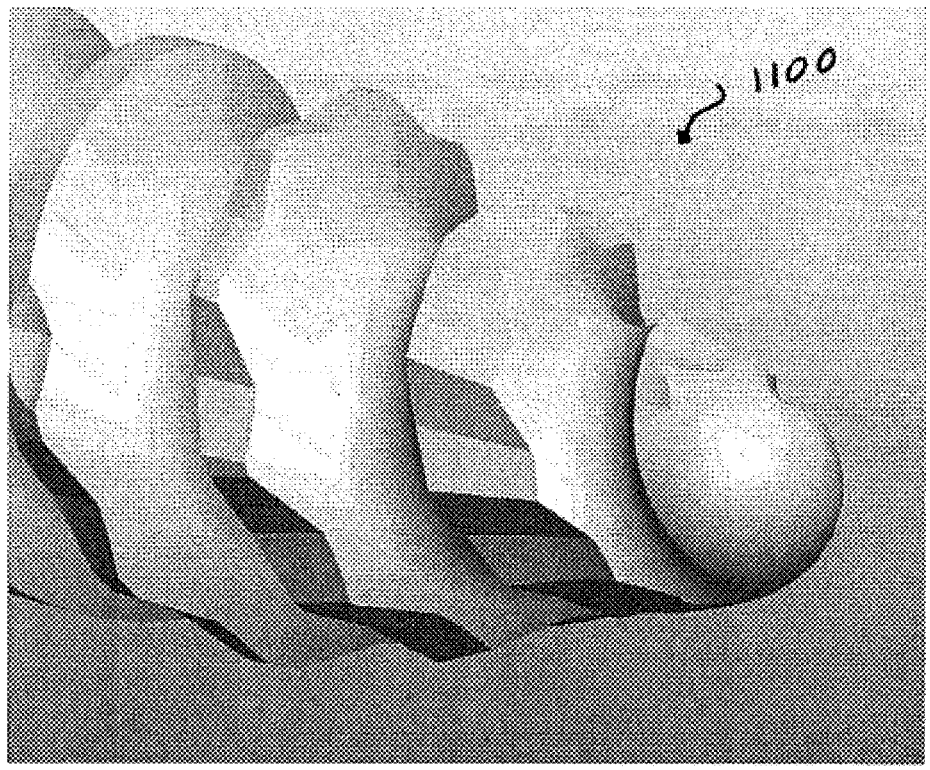
Figure 9I:
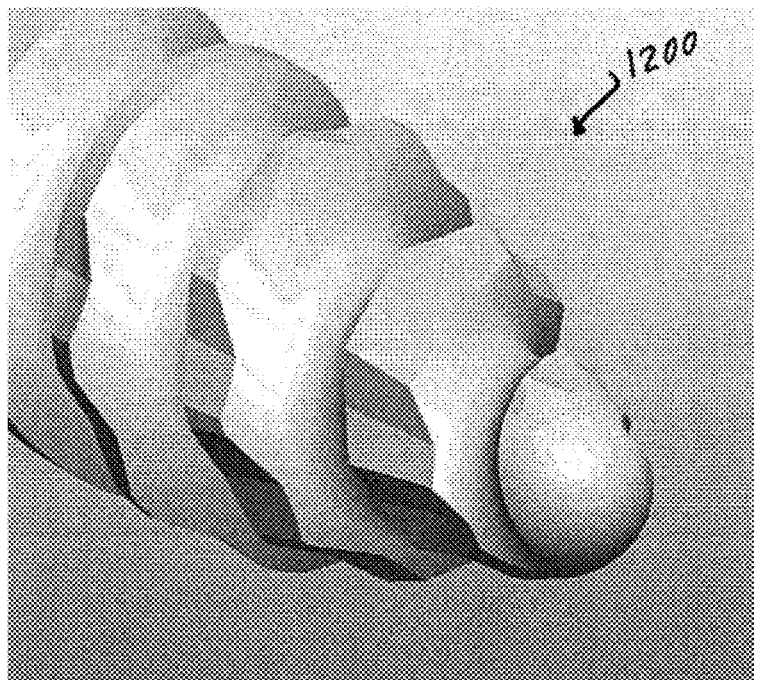

FIGS. 9A-9C depict fasteners having peaks of one type. For example, in FIG. 9C, peaks 612 are defined by a linear edge 613 at an abutment between surfaces connecting peak 612 with adjacent troughs. FIGS. 9D-9I depict fasteners having peaks of two types. For example, in FIG. 9F, certain peaks are defined by a linear edge, while peaks 919 are defined by a flat or planar surface at an abutment between surfaces connecting peak 919 with adjacent troughs. 13. In some embodiments, successive peaks along the serrated portion can alternate between the linear and planar peaks.

Figure 9J:
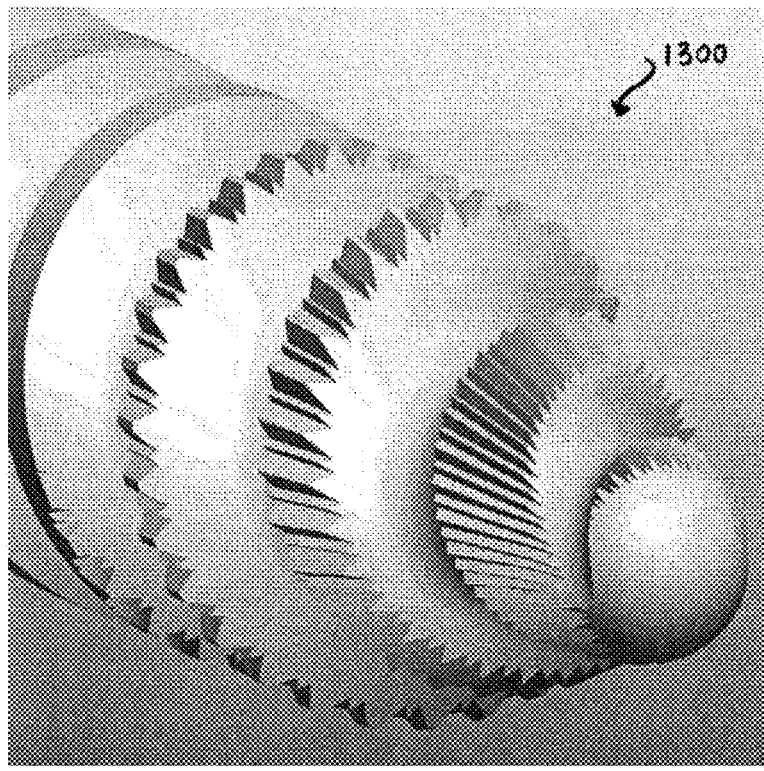

In another embodiment, shown in FIG. 9J, the threads include two types of peaks that alternate and differ in height, which is the distance from the longitudinal axis of the screw body to the top of the peak. This configuration forms a double-V cut and can vary with a first tall peak, adjacent to a first short peak, the first short peak adjacent to a second tall peak, the pattern (tall-short-tall-short) continuing around the threads. The taller peaks can have the same or different height, though both are preferable greater in magnitude than the heights of the shorter peaks, which can be the same or different.

Figure 9K:
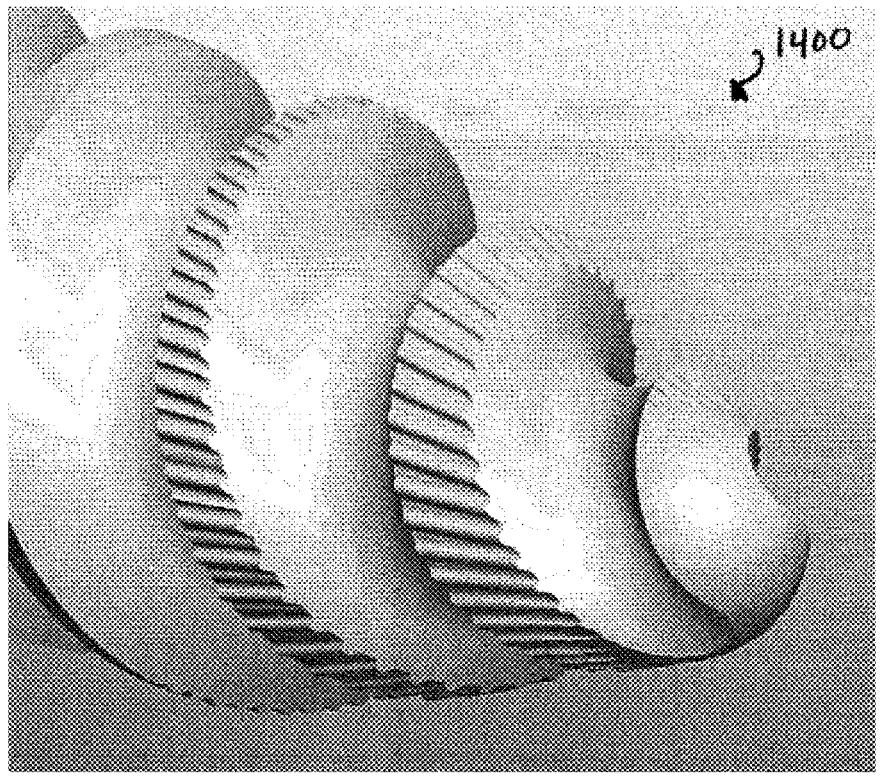
Figure 9L:
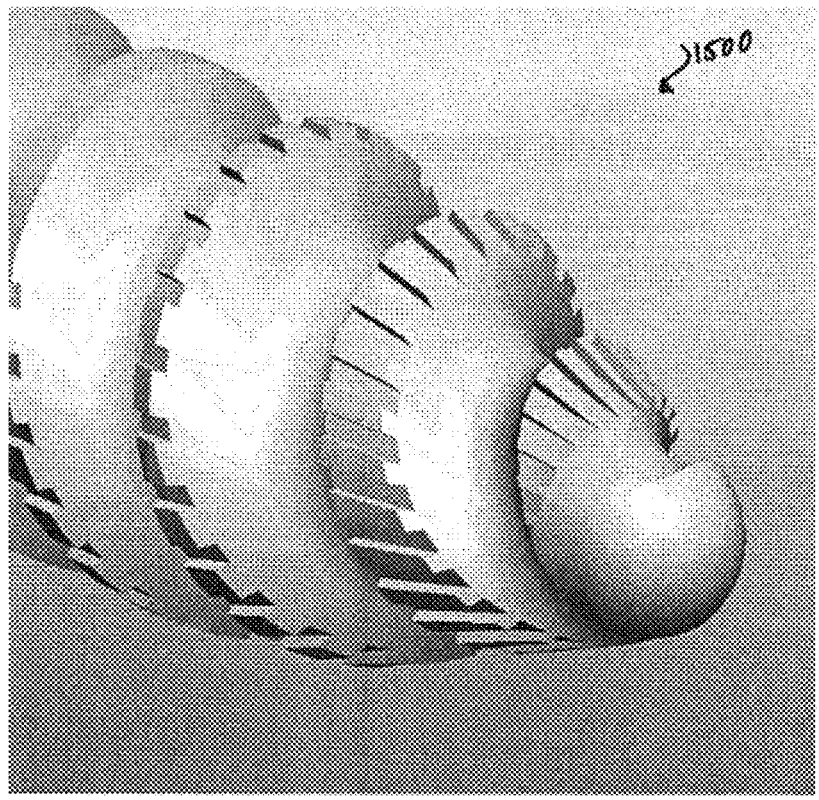
Figure 9M:
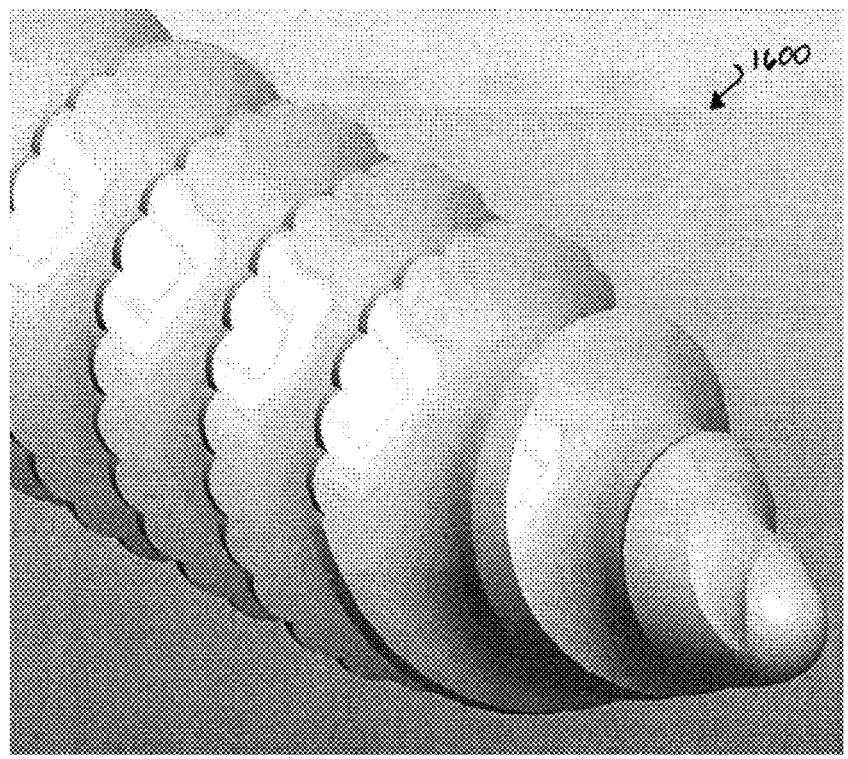

In another embodiment, shown in FIG. 9K, the peaks and troughs are rounded. In another embodiment, shown in FIG. 9L, the threads are square shaped or rectangular in cross-section, having two linear edges defining each peak and two linear edges defining each trough. In another embodiment, shown in FIG. 9M, the serrations are scalloped such that the peaks are curved with the troughs forming linear edges.

Figure 9N:
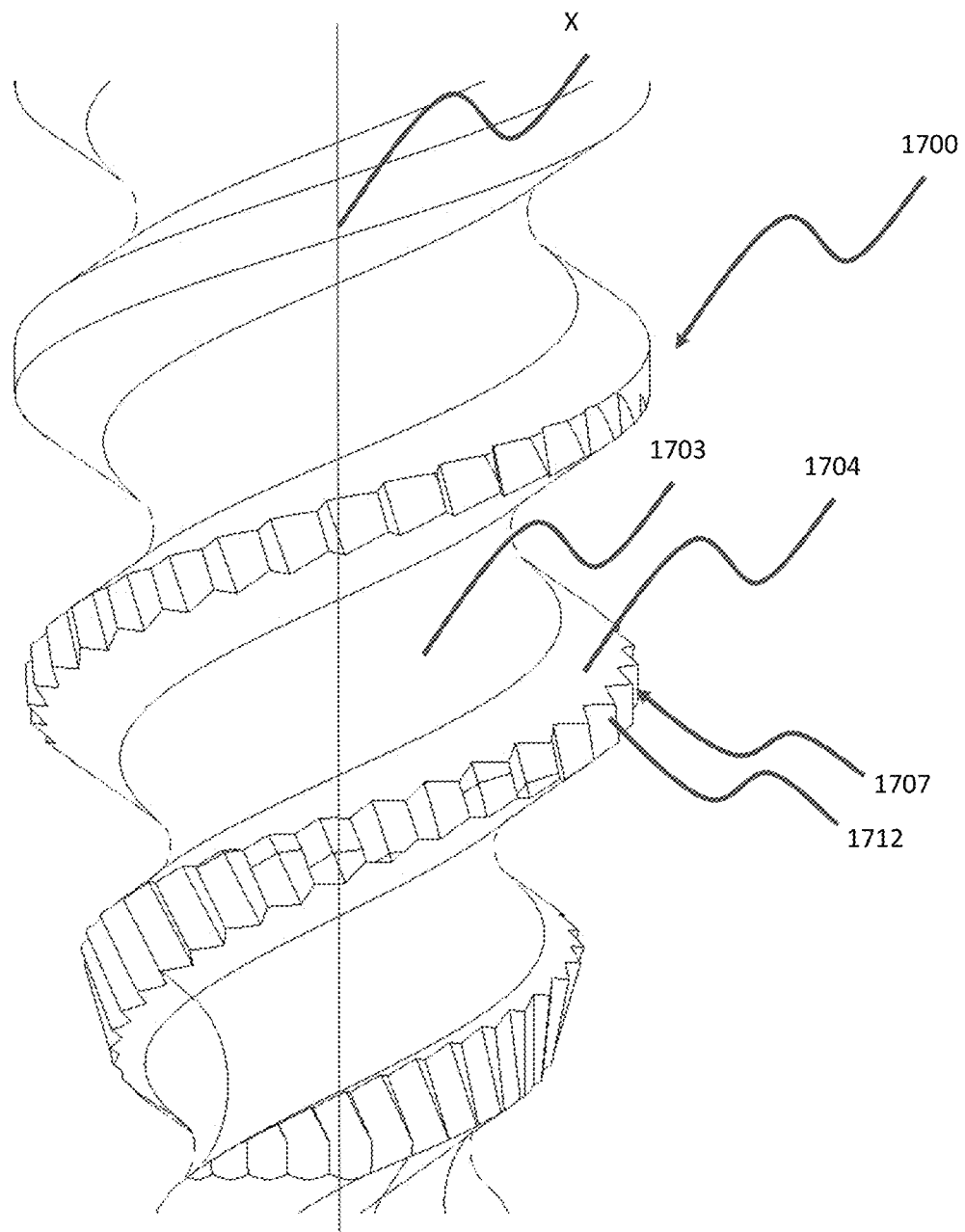
Figure 9O:
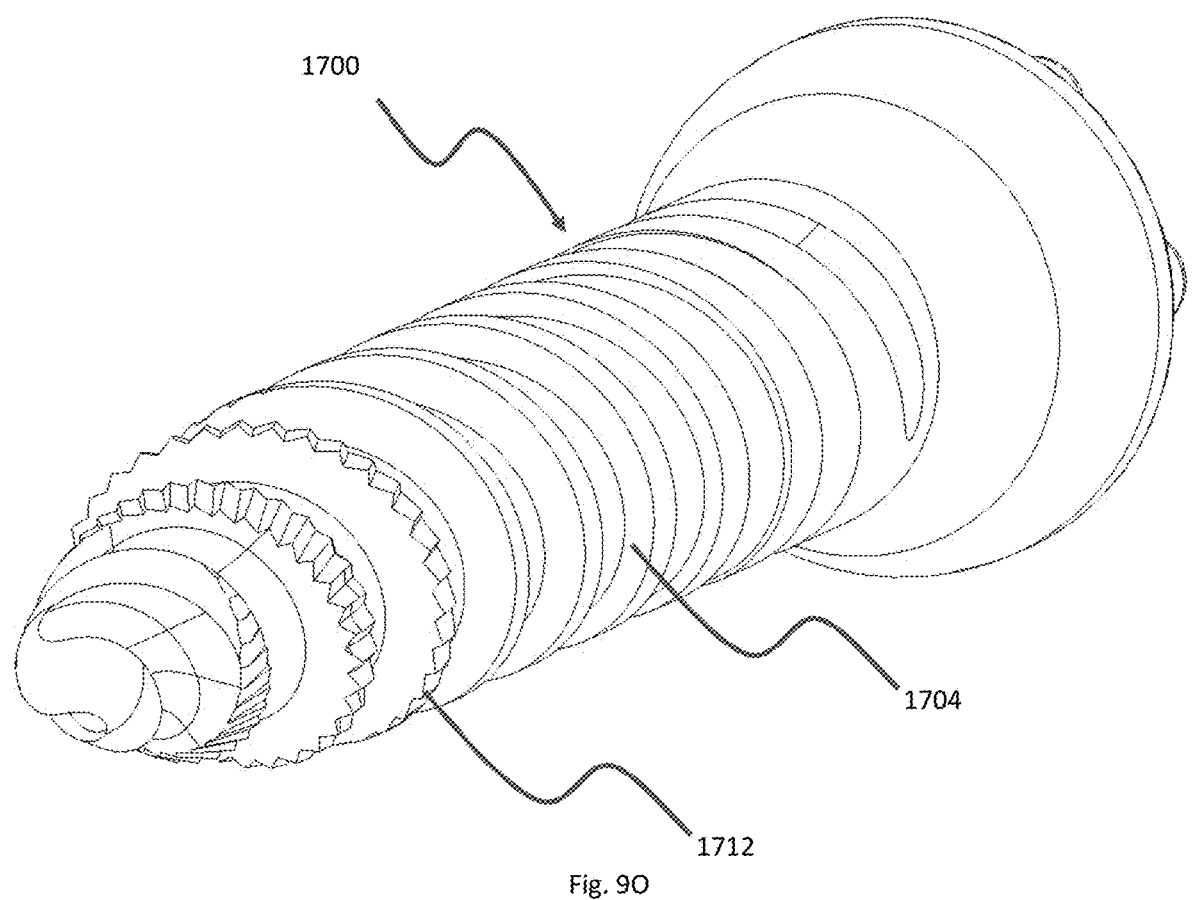

In another embodiment, shown in FIGS. 9N and 9O, the serrations can be helical in the opposite direction of the threads of a fastener 1700. That is, serrations 1707 can have peaks 1712 that extend along helical curves winding around fastener 1700 in a direction opposite to the helical curve along which thread 1704 extends. In this way, peaks 1712 are not aligned with or parallel to a longitudinal axis X of shaft 1703.

Figure 9P:
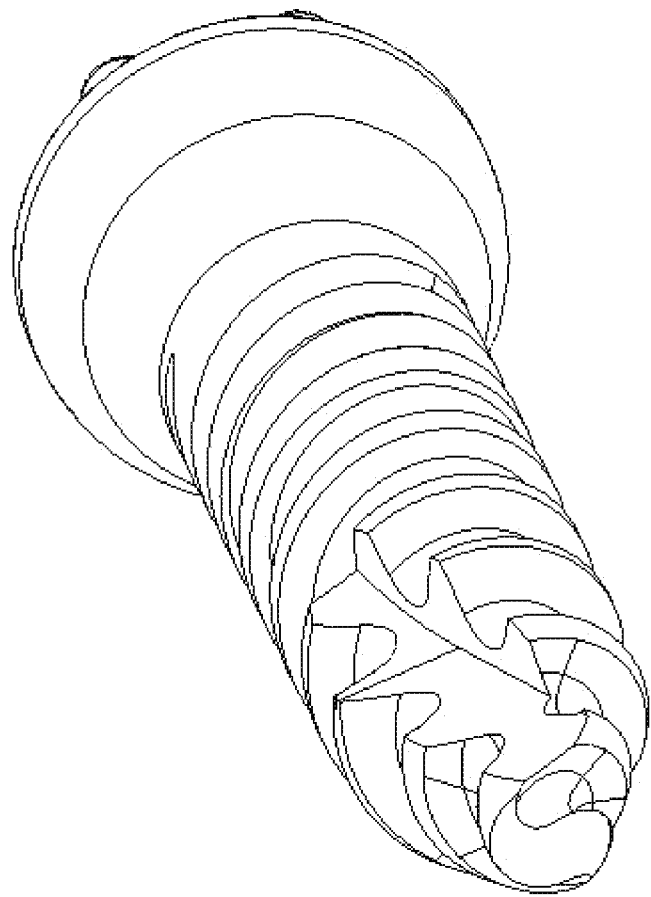
Figure 9Q:
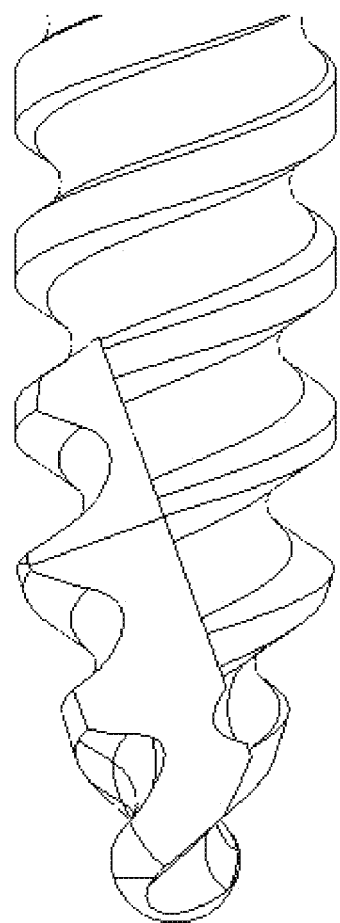

In another embodiment, shown in FIG. 9P, a fastener has a cutting flute that extends in a linear direction along an axis angled with respect to the longitudinal axis of the shaft. In another embodiment, shown in FIG. 9Q, a fastener has a cutting flute that extends along a helical path from a distal tip of the shaft. Fasteners according to the present embodiments can include single or dual lead threads and can include one or more cutting flutes. A dual lead provides the fastener with superior pullout strength.

Figure 10:
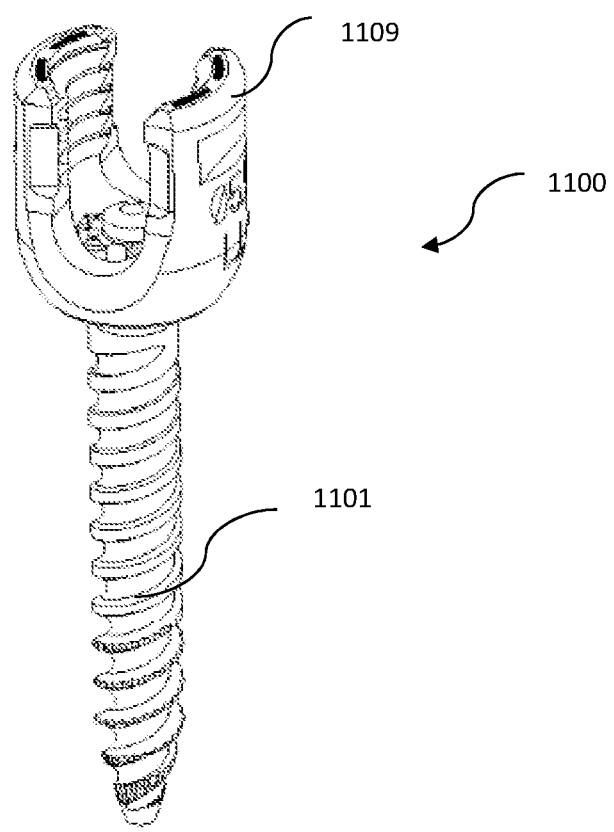
FIGS. 10-13 are perspective views of fastener in accordance with other embodiments of the present invention.
Figure 11:
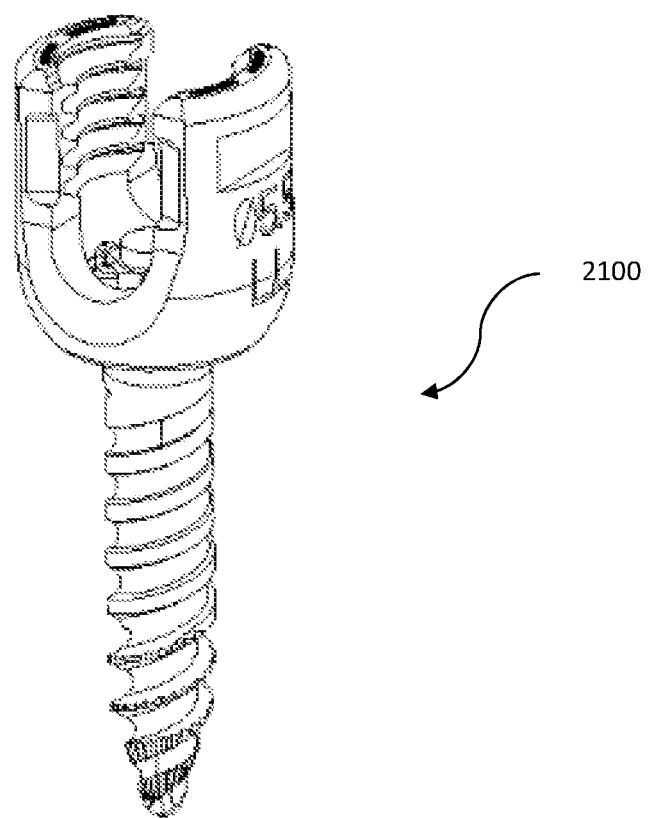
Figure 12:
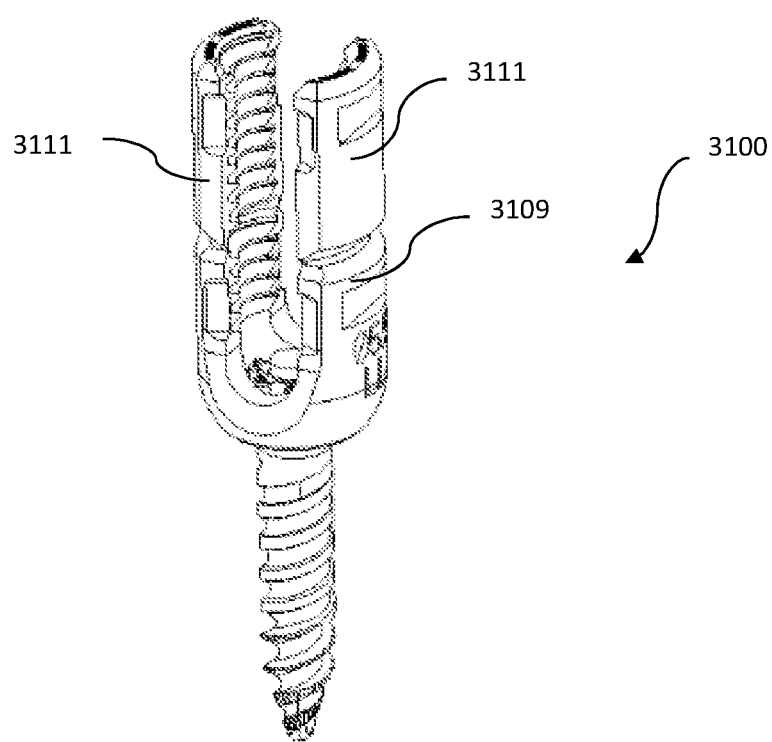
Figure 13:
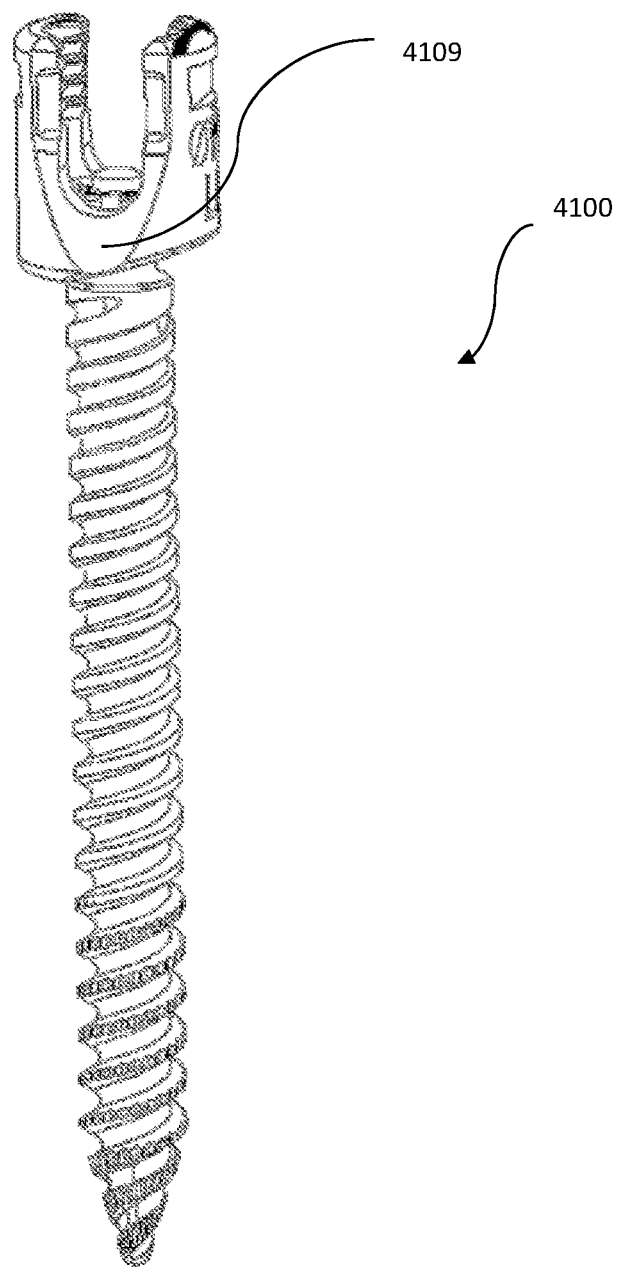

FIG. 10 depicts an embodiment similar to fastener 100 in which a fastener 1100 is shown with a screw body 1101 and a tulip 1109. FIG. 11 depicts an embodiment similar to that of FIG. 10, but one in which a fastener 2100 is not cannulated. An embodiment depicted in FIG. 12 is a fastener 3100 in which a tulip 3109 includes retractor blades 3111 that act as guides during insertion of a spinal rod and can be detached once the spinal rod is anchored to tulip 3109. FIG. 13 depicts an embodiment similar to fastener 100 in which a fastener 4100 has a longer shaft and a tulip 4109 is angled on its distal surface.

Experimental tests were run with different configurations of screws in accordance with the embodiments of the present invention. Each screw has a diameter of 5.0 mm and a length of 35.0 mm, and is further configured as follows:

| Screw A | Double Lead | Non-Cannulated | Cutting Flute | No Serrations |
| Screw B | Double Lead | Non-Cannulated | Cutting Flute | Serrations |
| Screw C | Double Lead | Cannulated | No Cutting Flute | Serrations |
| Screw D | Double Lead | Non-Cannulated | No Cutting Flute | Serrations |

Figure 14:
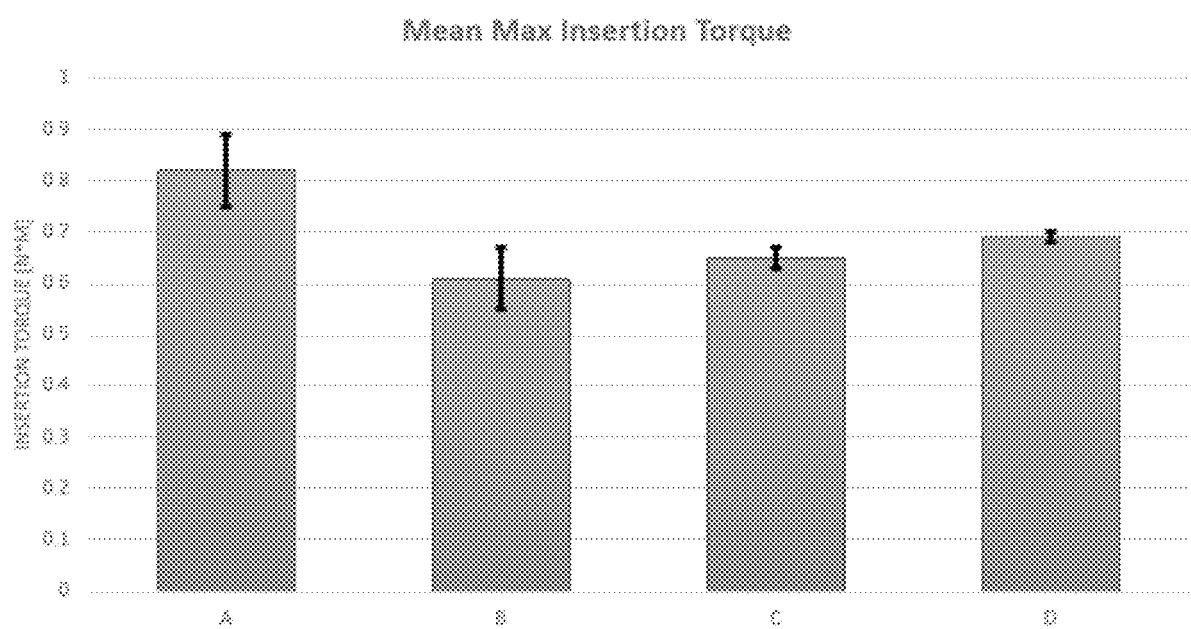
FIG. 14 is a chart of mean maximum insertion torque for different versions of fasteners in accordance with the present invention.

Screws A-D were tested to determine mean maximum insertion torque. As shown in FIG. 14, Screws B-D having serrations in accordance with the present invention showed superior performance to Screw A, which does not include serrations. The mean maximum insertion torque is less for all of Screws B-D as compared with Screw A. This evidences the desired result of lowering the insertion torque for a screw by providing serrations, to improve the performance of manual insertion.

In a serrated bone screw according to the present invention, the serrated portion can be defined as a function of thread length. Keeping the length of the serrated portion of the thread proportional to the thread length ensures consistent feel irrespective of screw length. By creating a proportional relationship, the end user will have the same experience despite the screw length. Calculating the length of the serrated portion can be done using the following formula: (Serration Length)=(Thread Length) times (X), where X equals a constant. This results in a linear relationship between the length of the serrated portion and the thread length. Thus, kits of screws in accordance with the present invention can include screws of different overall lengths having proportional serrated lengths based on a constant value.

In other embodiments, due to manufacturing constraints, it may be desirable to have fewer unique serration lengths, but still satisfy the need for a consistent feel. Accordingly, the serrated portion can be defined using a bucketed proportional approach. For example, if (Screw Length)≤(X) then (Serration Length)=(Y), where X is a defined Screw Length and Y is a defined Serration Length. This results in fewer unique serration lengths, but provides the same reduced insertion torque to the end user. For instance, by defining five (5) "buckets" of serration lengths, you can achieve a (Serration Length)/(Thread Length) proportion in a desired range, for example, 0.25 to 0.45. Kits of screws in accordance with the present invention can include screws of different lengths having serrated lengths according to these different "buckets" to provide multiple options for a user.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A kit comprising:
a plurality of fasteners configured for spinal applications, each of the plurality of fasteners comprising:
a head having a channel adapted to receive a spinal rod; and
a shaft extending from the head to a distal tip and having a thread, at least a portion of the thread being serrated,
wherein the serrated portion of the thread includes serrations having respective thicknesses measured parallel to a longitudinal axis of the shaft, successive thicknesses increasing in magnitude along a portion of a length of the thread toward the distal tip;
wherein the lengths of the respective threads of the plurality of fasteners are different, and
wherein for each fastener of the plurality of fasteners, a length of the serrated portion is proportional to the length of the thread by a value that is constant among the plurality of fasteners.

2. The kit of claim 1, wherein in at least one fastener of the plurality of fasteners, an angle between a sidewall of the thread and the longitudinal axis of the shaft varies along a length of the shaft.

3. The kit of claim 1, wherein in at least one fastener of the plurality of fasteners, at least a portion of the head is polyaxially movable with respect to the shaft.

4. The kit of claim 1, wherein in at least one fastener of the plurality of fasteners, the shaft is cannulated.

5. The kit of claim 1, wherein in at least one fastener of the plurality of fasteners, the shaft is tapered, and the tapered shaft is defined by an angle of between 16 and 20 degrees measured between the longitudinal axis of the shaft and an axis intersecting outer surfaces of the thread at two or more revolutions thereof.

6. The kit of claim 1, wherein in at least one fastener of the plurality of fasteners, the serrations have respective widths measured perpendicular to the longitudinal axis of the shaft, successive widths decreasing in magnitude along a portion of the length of the thread toward the distal tip.

7. The kit of claim 1, wherein in at least one fastener of the plurality of fasteners, the serrations have respective widths measured perpendicular to the longitudinal axis of the shaft, successive widths increasing in magnitude along a portion of the length of the thread toward the distal tip.

8. The kit of claim 1, wherein in at least one fastener of the plurality of fasteners, sidewalls of the thread that face one another form an angle therebetween of about 55 to 65 degrees.

9. The kit of claim 1, wherein in at least one fastener of the plurality of fasteners, the head is monoaxially attached to the shaft.

10. A fastener configured for spinal applications comprising:
- a head having a channel adapted to receive a spinal rod;
- a shaft coupled with the head, the shaft having a distal tip;
- a thread extending between the head and the distal tip; and
- a serrated portion extending along at least a portion of the thread, the serrated portion including peaks and troughs,
- wherein the peaks include a first type of peak defined by a linear edge at an abutment between surfaces connecting the peak with adjacent troughs and a second type of peak different from the first type of peak and defined by a planar surface at an abutment between surfaces connecting the peak with adjacent troughs.

11. The fastener of claim 10, wherein each peak is disposed at a radial distance from the longitudinal axis of the shaft that is greater than a radial distance from the longitudinal axis of the shaft to an adjacent trough, each peak having a thickness measured parallel to the longitudinal axis of the shaft that is less than a thickness measured parallel to the longitudinal axis of the shaft of an adjacent trough.

12. The fastener of claim 10, wherein successive peaks along the serrated portion alternate between the first type of peak and the second type of peak.

13. The fastener of claim 10, wherein the first type of peak varies in height along a length of the serrated portion and includes a first short peak with a first radius measured from the longitudinal axis of the shaft adjacent to a first tall peak with a second radius, which in turn is adjacent to a second short peak with a third radius, adjacent to a second tall peak with a fourth radius, the first and third radii being similar and both lesser in dimension than the second and fourth radii.

14. The fastener of claim 10, wherein the serrated portion includes a progressively increasing pitch from the tip toward the head.

15. The fastener of claim 10, wherein the peaks extend along helical curves winding around the shaft in a direction opposite to a helical curve along which the thread extends.

16. The fastener of claim 10, wherein the peaks extend along axes that are parallel to or aligned with a longitudinal axis of the shaft.

17. A kit comprising:
- a plurality of fasteners configured for spinal applications, each of the plurality of fasteners comprising:
  - a head having a channel adapted to receive a spinal rod; and
  - a shaft extending from the head to a distal tip and having a thread, at least a portion of the thread being serrated,
  - wherein the serrated portion of the thread includes serrations having respective thicknesses measured parallel to a longitudinal axis of the shaft, successive thicknesses increasing in magnitude along a portion of a length of the thread toward the distal tip;
- wherein the lengths of the respective threads of the plurality of fasteners are different, and
- wherein for each fastener in a first group of fasteners of the plurality of fasteners, a length of the respective serrated portion is equal to a first value, and for each fastener in a different second group of fasteners of the plurality of fasteners, a length of the respective serrated portion is equal to a second value different than the first value.

18. The kit of claim 17, wherein in at least one fastener of the plurality of fasteners, an angle between a sidewall of the thread and the longitudinal axis of the shaft varies along a length of the shaft.

19. The kit of claim 17, wherein in at least one fastener of the plurality of fasteners, at least a portion of the head is polyaxially movable with respect to the shaft.

20. The kit of claim 17, wherein in at least one fastener of the plurality of fasteners, the shaft is cannulated.

* * * * *